United States Patent [19]
Billet et al.

[11] Patent Number: 5,951,293
[45] Date of Patent: Sep. 14, 1999

[54] DENTAL PROSTHESIS WITH COMPOSITE SUPPORT SHELL AND COATING, PREIMPREGNATED FABRIC PART, MANUFACTURING METHOD AND MACHINE

[76] Inventors: Gilles Billet, 32, avenue d'Haussez, F-38500 Voiron; Bruno Clunet-Coste, Rue Tolvon, F-38960 Saint-Etienne-de-Crossey; Bernard Maneuf, Hameau de Vouise, F-38500 Voiron, all of France

[21] Appl. No.: 09/089,669

[22] Filed: Jun. 3, 1998

Related U.S. Application Data

[62] Division of application No. 08/619,732, filed as application No. PCT/FR94/01119, Sep. 26, 1994, Pat. No. 5,839,900.

[30] Foreign Application Priority Data

Sep. 24, 1993 [FR] France ................................. 93 11414

[51] Int. Cl.[6] ................................................ A61C 5/08
[52] U.S. Cl. ..................... 433/218; 433/222.1; 433/223
[58] Field of Search ................................. 433/218, 219, 433/215, 202.1, 217.1, 222.1, 223

[56] References Cited

U.S. PATENT DOCUMENTS

| | | |
|---|---|---|
| 2,755,552 | 7/1956 | Brandau ................................. 433/215 |
| 3,481,772 | 12/1969 | MacNairn et al. . |
| 4,504,229 | 3/1985 | Garito et al. ............................. 433/215 |
| 4,728,291 | 3/1988 | Golub ...................................... 433/215 |
| 4,793,809 | 12/1988 | Sigler et al. . |
| 4,846,718 | 7/1989 | Rieger . |
| 4,894,012 | 1/1990 | Goldberg et al. ........................ 433/215 |
| 5,062,799 | 11/1991 | Duncan et al. . |
| 5,104,591 | 4/1992 | Masuhara et al. . |
| 5,120,224 | 6/1992 | Golub . |
| 5,314,335 | 5/1994 | Fung . |
| 5,328,372 | 7/1994 | Reynaud et al. . |
| 5,538,429 | 7/1996 | Mayclin . |

FOREIGN PATENT DOCUMENTS

| | | |
|---|---|---|
| 432001 | 6/1991 | European Pat. Off. . |
| 2090395 | 1/1972 | France . |
| 2588181 | 10/1987 | France . |
| 2018666 | 10/1979 | United Kingdom . |
| 89/04640 | 6/1989 | WIPO . |

*Primary Examiner*—Nicholas D. Lucchesi
*Attorney, Agent, or Firm*—Oliff & Berridge, PLC

[57] ABSTRACT

A fabric part preimpregnated with a matrix before hardening designed to form, after shaping, hardening and depositing of an external finishing coating, a support shell of a dental prosthesis. The matrix has at least one component of the same nature as at least one component of the coating.

8 Claims, 2 Drawing Sheets

DENTAL PROSTHESIS WITH COMPOSITE SUPPORT SHELL AND COATING, PREIMPREGNATED FABRIC PART, MANUFACTURING METHOD AND MACHINE

This is a Division of Application Ser. No. 08/619,732 filed Mar. 22, 1996 (U. S. National Stage of PCT/FR94/01119 filed Sep. 26, 1994), now U.S. Pat. No. 5,839,900. The entire disclosure of the prior application is hereby incorporated by reference herein in its entirety.

FIELD OF THE INVENTION

The invention relates to a dental prosthesis such as a crown, a bridge, an implanted prosthesis, an artificial tooth or removable appliance, i.e. a prosthesis intended to reconstitute the shape and characteristics of at least one tooth from a natural stump (a crown fitted in the mouth on the original tooth), an implant abutment (a crown fitted on an implant in the mouth) or laboratory model representative of the soft tissues (denture).

BACKGROUND

Known dental prostheses are achieved in the form of a framework in a single part made of metal or composite material (WO-A-8,904,640) or resin, or with a generally metallic shell or armature covered with ceramic or resin. Also FR-A-2,588,181 recommends the use of composite material to achieve posts for inlays cores, shells, bridges or implants.

In the former art, it was always sought to manufacture these prostheses, and more particularly their internal constituting elements (shells, metallic frameworks, posts, shells . . . ), from as rigid materials as possible. Thus, WOA-8,904,640 recommends that dental prostheses be manufactured from a composite material with a greater rigidity and strength and more generally with higher mechanical characteristics than those of the polymers generally used. More particularly, this document recommends that a composite material with an elasticity modulus higher than 3.45 GPa be used. Also, FR-A-2,588,181 recommends the use of composite materials reinforced by high strength fibers, notably carbon fibers with a matrix more particularly made of epoxy resin or polyester in order to give the prosthesis a high stiffness. The well-known essential qualities of a tooth or of a dental prosthesis are in fact on the one hand not to break due to the effect of impacts and on the other hand not to wear too quickly. But up to now it has essentially been sought to strengthen the rigidity of the prostheses in order to achieve these qualities.

Nevertheless, entirely metallic prostheses are unaesthetic, prostheses made entirely from resin prove fragile in use, those achieved by a metallic shell or armature covered with ceramic are extremely costly, long and delicate to manufacture, and those achieved from a metallic framework or armature covered with a resin are also long to manufacture and subject to deterioration in use on account of the poor adherence of the resin on the metal armatures or shells and of the concentration of the stresses at the interfaces of materials having very different mechanical characteristics (metal/resin).

SUMMARY OF THE INVENTION

The inventors have however determined that to have satisfactory mechanical qualities, a dental prosthesis must imitate or reproduce as close as possible the natural tooth which comprises a pulp cavity surrounded by dentin and an enamel coating. Thus, it is important that the prosthesis be made up of two distinct parts whose mechanical characteristics are different, i.e. a hard coating resistant to abrasion, and a support shell or armature whose characteristics are determined in such a way that the hard coating does not break, and that it be rigidly associated to the stump while reproducing the dynamic and static mechanical characteristics of the natural tooth.

Accordingly it is an object of the present invention to propose a dental prosthesis comprising a support shell and an external finishing coating covering this support shell which does not present the above-mentioned shortcomings of the state of the technique, i.e. with which the coating adheres perfectly to the support shell, the respective mechanical and physico-chemical characteristics of the coating and support shell being able to be determined independently from their respective stresses proper.

Another object of the present invention is to propose a dental prosthesis which reproduces the mechanical characteristics of the natural tooth as far as possible, and which is in addition biocompatible and easy to manufacture.

A particular object of the present invention is to propose a dental prosthesis which is perfectly resistant to wear, which does not break with use, and which is compatible with the biological environment of the tooth, notably which protects the bone against impacts and prevents osteolysis or unsealing or unsticking phenomena, notably at the level of the collar of the tooth.

Still another object of the present invention is to propose such a dental prosthesis which enables the patient's proprioceptive sensations to be preserved as far as possible.

Still another object of the present invention is to propose a dental prosthesis which meets aesthetic requirements and the state of whose surface can imitate that of a natural tooth.

Still another object of the present invention is to propose such a prosthesis which at the same time does not contain any metal.

Still another object of the present invention is to propose a fabric part preimpregnated with a organic matrix before cross-linking designed for manufacture of a prosthesis according to the invention.

Still another object of the present invention is to propose a machine for implementation of this method. More particularly, an object of the invention is to propose a particularly simple, inexpensive, compact machine, which can be proposed to prosthesists at low cost.

To achieve this, the invention relates to a dental prosthesis comprising a support shell intended to cover a natural, implant or artificial stump, and an external finishing coating covering the support shell characterized in that the support shell is comprised of a composite material comprising a fiber armature sunk in an organic matrix, and in that the external finishing coating is comprised of at least one layer of organic resin at least one essential component of which is of the same nature as at least one essential component of the organic matrix of the support shell. The combined use of a composite material for the support shell and of an organic resin of the same nature for the coating enables the mechanical characteristics (elasticity modulus, elastic limit, tensile and compressive strength, . . . ) of both the support shell and the coating to be adapted independently from one another, while ensuring a perfect cohesion of the coating on the support shell and an adhesion without any possible dissociation.

According to the invention the main component(s) of the cosmetic resin and of the organic matrix are similar or identical. More particularly and according to the invention the matrix of the support shell and external finishing coating are essentially formed by at least one methacrylate resin, notably a dimethacrylate resin. According to the invention, a resin can be used formed by BIS phenol A derivatives, notably BIS-GMA (BIS-phenol A-glycidyl dimethacrylate). Any other organic resin can be used provided that it is biocompatible, that it enables a coating and a composite material matrix to be achieved suitable to provide the required mechanical characteristics, and that the presence of at least one common component in the matrix and in the resin of the coating enables a cohesion and a strong adhesion on each other by chemical interaction.

According to the invention, the elasticity modulus of the support shell is never different from that of the natural crown or root dentin by ±25%. More particularly, and according to the invention, the elasticity modulus of the support shell is lower than or equal to 25 GPa, notably comprised between 7 and 25 GPa whereas the elasticity modulus of the coating is higher than 10 GPa, notably comprised between 12 and 26 GPa. Furthermore, the support shell has a tensile strength greater than 120 MPa, notably about 200 MPa, and a compressive strength comprised between 300 and 400 MPa. The external finishing coating moreover has a hardness greater than 100 KHN.

According to the invention, the armature of the support shell is comprised of at least one layer of fiber-meshed fabric, notably of a laminate comprised of a plurality of layers of fiber-meshed fabric, with notably glass, ceramic or silica fibers.

The invention also relates to a fabric part preimpregnated with an organic matrix before cross-linking designed to form, after shaping, cross-linking and placing of an external finishing coating made of organic resin, a dental prosthesis according to the invention, characterized in that the organic matrix has at least one essential component of the same nature as at least one essential component of the coating. According to the invention, this part is in the general shape of a disk securedly held between two films or membranes and/or predeformed with its central part at least appreciably conical. The fabric part can also be of any shape, the user then being able to cut the part according to the application he intends to make thereof, notably to form the link between two or more support shells to constitute a bridge or denture.

The invention also relates to a method for manufacturing a dental prosthesis according to the invention, characterized in that a preimpregnated fabric part according to the invention is placed on a shaping model, the preimpregnated fabric part is shaped on the shaping model by compression, cross-linking of the organic matrix of the preimpregnated fabric part is performed to obtain the rigid support shell, and successive layers of organic resin are achieved cross-linked on the support shell to form an external finishing coating. The organic resin which is deposited in successive layers to form the coating comprises at least one essential component of the same nature as an essential component of the matrix of the preimpregnated fabric.

And the invention also relates to a machine for implementation of the method according to the invention, characterized in that this machine comprises a tight enclosure, a plate for receiving a shaping model in the enclosure, a flexible membrane which is in general fluid-proof and for example air-tight, separating the enclosure into two chambers, means for creating a lower fluid pressure in the chamber containing the shaping model than in the other chamber and means for cross-linking the parts placed on the shaping model.

The invention also relates to a dental prosthesis, a preimpregnated fabric part, a manufacturing method and a machine comprising in combination all or part of the features mentioned above or hereafter.

BRIEF DESCRIPTION OF THE DRAWINGS

Other features and advantages of the invention will become more clearly apparent from the following description which refers to the accompanying drawings in which.

DETAILED DESCRIPTIONS OF THE PREFERRED EMBODIMENTS

Figure 1:
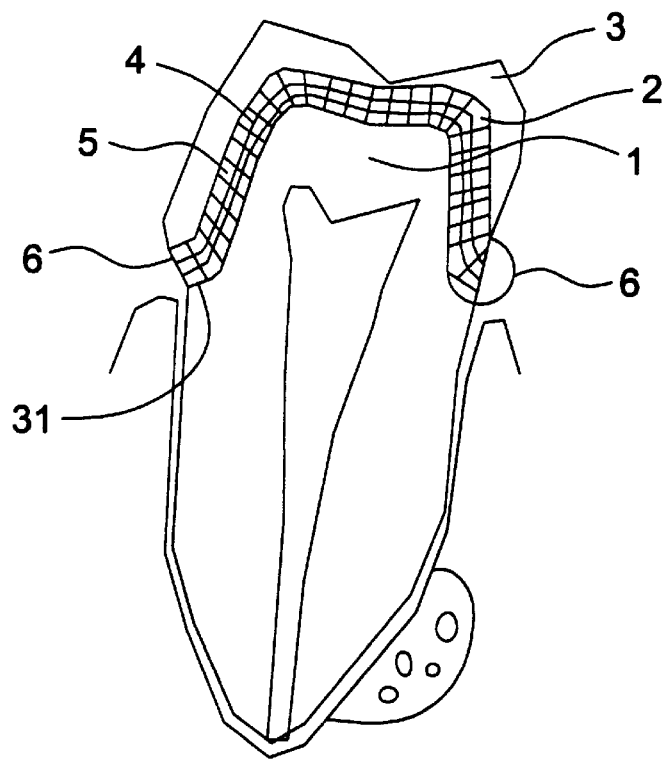
FIG. 1 is a vertical sectional view of a tooth equipped with a dental prosthesis according to the invention.

In FIG. 1, a dental prosthesis according to the invention has been represented fitted on a natural stump 1 of dentin trimmed in the mouth to receive the prosthesis. This prosthesis is formed by a support shell 2 covering the natural stump 1 and an external finishing coating 3 covering the support shell 2. The support shell 2 is composed of a composite material comprising an armature of fibers 4 sunk in an organic matrix 5. And the coating 3 is composed of at least one layer of organic resin at least one essential component of which is of the same nature as at least one essential component of the organic matrix 5 so that this organic resin adheres by chemical interaction on the composite material of the support shell 2.

Throughout the text, "essential component" is taken to mean a component whose concentration in the matrix or the resin is greater than 10%, and the expression "of the same nature" is taken to mean the fact that the components are identical or that they belong to the same chemical family so that they can interact with one another forming a solid homogeneous structure after cross-linking.

According to the invention, the organic resin of the coating and the matrix of the support shell therefore have at least one component in common. Preferably and according to the invention, the main component(s) of the resin and of the matrix are of the same nature, notably similar or identical.

Any sort of organic resin constituting the coating and of composite materials constituting the support shell 2 can be used provided that the resulting prosthesis has satisfactory mechanical characteristics meeting the aesthetic and bio-compatibility requirements. Nevertheless, the organic resins used for the dental finishing coating are generally resins composed of an organic base and of charges or micro-charges. According to the invention, the organic matrix constituting the support shell 2 is also an organic resin made up of the same base as that of the coating 3, and of suitable fillers or microcharges to facilitate its implementation and give it suitable mechanical characteristics.

According to the invention, the matrix 5 of the support shell 2 and the external finishing coating 3 are essentially made up of at least one methacrylate resin, notably a dimethacrylate resin.

According to the invention, the matrix of the support shell 2 comprises at least one essential component chosen from the group formed by the dimethacrylate-base aromatic resins, the epoxy-base aromatic resins and the polymethacrylate resins. According to the invention, the matrix 5 can also comprise urethane methacrylate resins. Among the dimethacrylate aromatic resins, BIS phenol A derivatives can notably be used, such as bisphenol A-glycidyl-dimethacrylate (BIS-GMA) and/or other monomers such as urethane-dimethacrylate (UDMA) and/or a triethyleneglycol-dimethacrylate (TEDMA).

According to the invention, a BIS-GMA-base resin can be used modified by copolymerization with composites of lower molecular weight, notably as non-restrictive examples bisphenol glycidyl-dimethacrylates (BIS-MA), bisphenol ethyl-methacrylates (BIS-EMA), bisphenol propyl-methacrylates (BIS-PMA), ethylene glycol-dimethacrylates (EGDMA), diethylene glycol-dimethacrylates (DEGDMA), triethylene glycol-dimethacrylates (TEGDMA), triethylene glycol-methacrylates (TEGMA), methyl-methacrylates (MMA), and polyurethane-fluor-methacrylates (PFUMA).

The organic matrix 5 making up the support shell 2 also comprises charges and notably light-curing components such as dicetones, notably diacetyl and/or quinones such as camphoro-quinone and acenaphtene quinone sensitive to visible light and also accelerators, notably amines. Thus, the organic matrix according to the invention can be cross-linked by lighting in visible light.

Furthermore, the composite material of the support shell 2 comprises an armature of fibers 4 composed of at least one layer of fiber-meshed fabric. According to the invention, the composite material of the support shell 2 is a laminate composed of a plurality of layers of fiber-meshed fabric, notably glass, ceramic or silica fibers. From two to ten layers of glass fiber fabric E or S each having a thickness of 0.1 mm can thus be used.

As a non-restrictive example, a fiber-meshed fabric having the following characteristics has given good results:
Weight: 90±5 g/m$^2$
Armature: satin of 4
Composition:
  warp: EC 5 22
  weft: EC 5 22
Thickness of the laminate per fold: 0.09 mm
Elasticity modulus:
  warp: about 18,000 MPa
  weft: about 18,000 MPa
Tensile strength:
  warp: 200 MPa
  weft: 200 MPa
For a laminate with 50% volume reinforcement.

Also, in addition to the fiber armature 4, the composite material according to the invention also comprises other inorganic charges. In particular, charges can be incorporated designed to modify the fluidity and pegosity of the matrix 5 such as silica-base particles whose diameter can vary at least from 0.1 $\mu$m to 100 $\mu$m, for example pyrolitic silica, and/or glass or ceramic-base particles, notably glass or borosilicate particles, ceramic glasses, barium-aluminium particles, strontium-aluminium particles, . . . Also, radio-opaque heavy metals can be incorporated, such as niobium, tin, titanium, etc, and also organic or mineral pigments designed to ensure the aesthetic aspect of the shell. Moreover, all these inorganic charges (particles and fibers) are treated before being incorporated in the organic matrix 5 by means of organo-silane composites such as aryloxy-silanes and/or halosilanes.

According to the invention, the support shell 2 comprises between 40 and 80% organic matrix volume. This means that the aromatic resin base components and the light-curing organic charges are comprised in a proportion between 40 and 80% of the composite material volume. And the inorganic charges, i.e. the armature 4 of fibers and the other inorganic charges are comprised between 20 and 60% of the composite material volume.

Furthermore, the external finishing coating 3 can be formed by a filled cosmetic resin, notably of the type formed by BIS-phenol-A derivatives such as BIS-GMA charged in such a way that it has a high rigidity, a great resistance to abrasion and a colour shade close to that of the natural tooth. Charged cosmetic resins of this kind are known as such.

The invention also relates to a dental prosthesis comprising a support shell 2 designed to cover a natural, implant or artificial stump 1, and an external finishing coating 3 covering the support shell 2, characterized in that the elasticity modulus of the support shell 2 is never different from that of the natural crown or root dentin by ±25%. According to the invention, the elasticity modulus of the support shell 2 is less than or equal to 25 GPa, notably comprised between 7 and 25 GPa, and the elasticity modulus of the external finishing coating 3 is greater than 10 GPa, notably comprised between 12 and 26 GPa. In this way, the interruption of continuity of the elasticity moduli between the different layers of materials existing in known prostheses of the state of the technique is eliminated. The reconstituted tooth obtained with the dental prosthesis according to the invention as represented in FIG. 1 therefore has similar mechanical characteristics to those of a natural tooth.

Moreover, the support shell 2 has a tensile strength greater than 120 MPa, notably about 200 MPa. This tensile strength is particularly great at the level of the neck 6 of the support shell 2 which, in practice, has to withstand tensile stresses. In addition, and according to the invention, the support shell 2 has a compressive strength comprised between 300 and 400 MPa to withstand the compression stresses generated by chewing. The external finishing coating 3 has a hardness greater than 100 KHN.

These respective mechanical characteristics of the finishing coating 3 and support shell 2 can easily be obtained with a suitable choice of the elements making up the composite material constituting the support shell 2 and the organic resin of the coating 3. In particular, the proportion of glass fibers and the number of layers of fabric used, as well as the diameter of the glass fibers influence the elasticity modulus in a manner known in itself.

Furthermore, according to the invention, the external finishing coating 3 adheres to superficial fibers of the armature 4 of fibers of the support shell 2 which are flush with or protrude out from the organic matrix 5 at the external surface of the support shell 2. In this way, the resin forming the coating 3 adheres directly on the fibers of the armature 4 which appear on the surface, which improves the cohesion and adhesion. Thus, from all the foregoing, it can be understood that the cohesion and adhesion between the external finishing coating 3 and the support shell 2 is achieved internally due to the existence, in combination, on the one hand of a physical fastening due to the penetration of the external finishing coating 3 into the network of superficial fibers of the armature 4 of fibers of the support shell 2, and on the other hand of a chemical interaction between the organic matrix 5 of the support shell 2 and the organic resin of the external finishing coating 3.

According to the invention, the first layer of organic resin of the coating 3 in contact with the support shell 2 is constituted by a resin formed by the common component(s) of the coating 3 of the organic matrix 5, i.e. by an unfilled resin. In particular, the first layer is comprised solely of non-charged methacrylate or dimethacrylate resin. This first layer of non-charged resin therefore penetrates into the composite material making up the support shell 2 on one side and into the first layer of charged resin of the coating 3 on the other side. A homogeneous mixture and a good continuity are thus obtained due to the solution between the support shell 2 and the coating 3.

The support shell 2 is itself fitted on the stump 1 by means of a luting cement 31 which is also organic resin-based, notably a 4-methacryloxyethyltrimellitic anhydride, activated by tri-n-butyl compound which provides the tightness between the stump 1 and prosthesis (resins called META4).

The tooth fitted with a dental prosthesis according to the invention therefore comprises, from the outside to the inside, a cosmetic external finishing coating 3 having a thickness comprised between 0 and 2 mm, a support shell 2 made of composite material whose thickness can vary between 0.1 and 2 mm, a layer of sealing cement 31 whose thickness also varies between 5 and 35 $\mu$m, and the stump 1 of natural dentine or reconstituted dentin of composite or metallic material.

The composite material of the support shell 2 can be made up of fibers other than glass, for example aramide (notably Kevlar, a registered trademark), carbon, boron, silica or ceramic fibers, etc. The organic matrix can also be a matrix which is cross-linked not by light but by a thermal or chemical or other process. The orientation, dimensions, and meshing of the fibers constituting the armature 4 are chosen according to the above-mentioned mechanical characteristics required according to the application of the prosthesis. According to the invention, the collar 6 of the support shell 2 has a thickness which is the same as the standard thickness of the support shell 2 elsewhere than at the collar 6. In addition, the meshing of the armature of fibers can be strengthened and tightened near the collar 6 in order to increase the tensile strength of the composite material at this place of the prosthesis. It has in fact been determined that the greatest stresses to which the prosthesis is subjected are generally situated at the level of the collar 6.

The invention also enables bridges to be achieved using two prostheses according to the invention joined by a joining element linking the two support shells 2. The joining element can itself be formed by a composite material or a material strengthened by a fabric or fibers.

The invention also relates to a fabric part 7 preimpregnated with an organic matrix before cross-linking which is designed to form after shaping, cross-linking and depositing of an external finishing coating 3 made of organic resin, a support shell 2 of a dental prosthesis according to the invention. The part 7 according to the invention is characterized in that the organic matrix has at least one essential component of the same nature as at least one essential component of the coating 3. The fabric part 7 is ready for use to form the support shell 2 of the prosthesis according to the invention after it has been cross-linked. It therefore comprises all the components which make up the support shell 2 of the prosthesis according to the invention. Thus, the main component(s) of the resin of the coating 3 and of the matrix of the part 7 are similar. The organic matrix of the part 7 and the resin forming the coating are also constituted by at least one methacrylate resin, notably a dimethacrylate resin. The fabric armature 4 of the part 7 is composed of at least one layer of fiber-meshed fabric, notably of a plurality thereof, more particularly between 2 and 10 layers of fiber fabric each having a thickness of about 0.1 mm. Preferably, and according to the invention, glass, ceramic or silica fibers are used.

According to the invention, the part 7 has the general shape of a disk with a diameter of 10 to 100 mm securedly held between two protective films 8 and/or between two flexible membranes 9, 10. The fabric part can also be of any shape, the user then being able to cut the part out according to the application he intends to make thereof notably to constitute the link between two or more support shells to constitute a bridge or denture.

The invention also relates to a manufacturing method of a dental prosthesis according to the invention from a preimpregnated fabric part 7 according to the invention. According to the invention, a preimpregnated fabric part 7 is placed on a shaping model 11 which can be either a reproconvion of a natural stump, or an implantable stump, or a model of a mobile prosthesis (for example in the case of manufacture of a denture). The preimpregnated fabric part 7 is then shaped on the shaping model 11 by compression by pressing this fabric part 7 onto the shaping model 11. Cross-linking of the organic matrix 5 of the preimpregnated fabric part 7 is then performed to obtain the rigid support shell 2. Successive layers of cross-linked organic resin are then made on the support shell 2 to form an external finishing coating 3. According to the invention, to form the preimpregnated fabric part 7 on the shaping model 11, and press it against this shaping model 11, a flexible fluid-proof membrane 9, notably air-tight, is applied by differential pressure of the fluid on the part 7 which is pressed against the shaping model 11. During this stage, to avoid the presence of one or more fluid pockets trapped between the shaping model 11 and membrane 9, the membrane 9 is moved progressively and longitudinally downwards or upwards over the surface of the shaping model 11 by application of a controlled differential pressure difference. The part 7 can be preformed with its central part at least appreciably cone-shaped before being placed on a model 11 in the form of a stump. In this way, the cone-shaped central part rests on the stump 11, without requiring specific securing means. As an alternative embodiment, the preimpregnated fabric part 7 can be placed and shaped on the shaping model 11 by holding it securedly between two flexible fluid-proof membranes 9, 10, and by applying the assembly thus formed by differential fluid pressure so as to press it against the shaping model 11. The base plate on which the artificial teeth will be placed is manufactured in a single operation. The first alternative embodiment described above is more preferably applicable in the case of manufacture of a unitary dental prosthesis.

According to the invention, the external surface 12 of the support shell 2 is subjected after cross-linking to an abrasion or an erosion before the first layer of organic resin designed to form the coating 3 is deposited to make the fibers of the fabric armature 4 appear at the surface. In this way, the subsequent layer deposited which constitutes the first layer forming the coating 3 comes into direct contact with the fibers of the armature 4. And according to the invention, the first layer of organic resin deposited on the support shell 2 is constituted by a resin formed by the common component (s) of the coating 3 and organic matrix 5, i.e. a non-charged or lightly charged resin.

Figure 2:
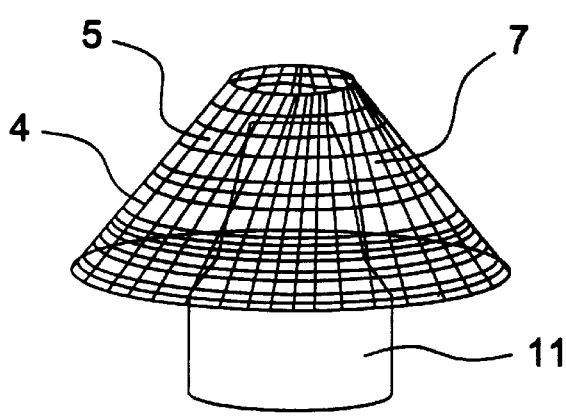
FIG. 2 is an elevational view of a preimpregnated fabric part according to the invention in the course of a stage of the manufacturing method according to the invention.
Figure 3:
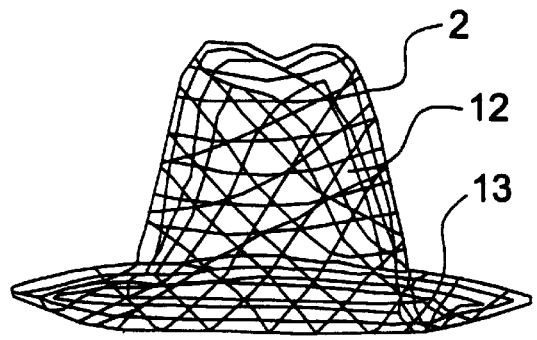
FIG. 3 is a similar view to FIG. 2 illustrating a subsequent stage of the manufacturing method according to the invention.

FIG. 2 represents the preimpregnated fabric part 7 preformed in a general cone shape placed on the shaping model 11 which is an artificial stump reproducing a natural stump. FIG. 3 represents the result obtained after the impregnated fabric part 7 has been shaped on the stump 11 by differential pressure. Starting from the stage in FIG. 3, the excess neck 13 of the support shell 2 is cut off, which absolutely must be performed before the stump is extracted. The rigid support shell 2 thus formed is then extracted either by simply separating it from the stump 11 if an isolating film has been placed between the stump 11 and the impregnated fabric part 7, or by chemical dissolution of the material making up the stump 11. An abrasion of the external surface 12 of the support shell 2 is then performed and successive photopolymerized layers of cosmetic resin are made to achieve the coating 3 as indicated above.

Figure 4:
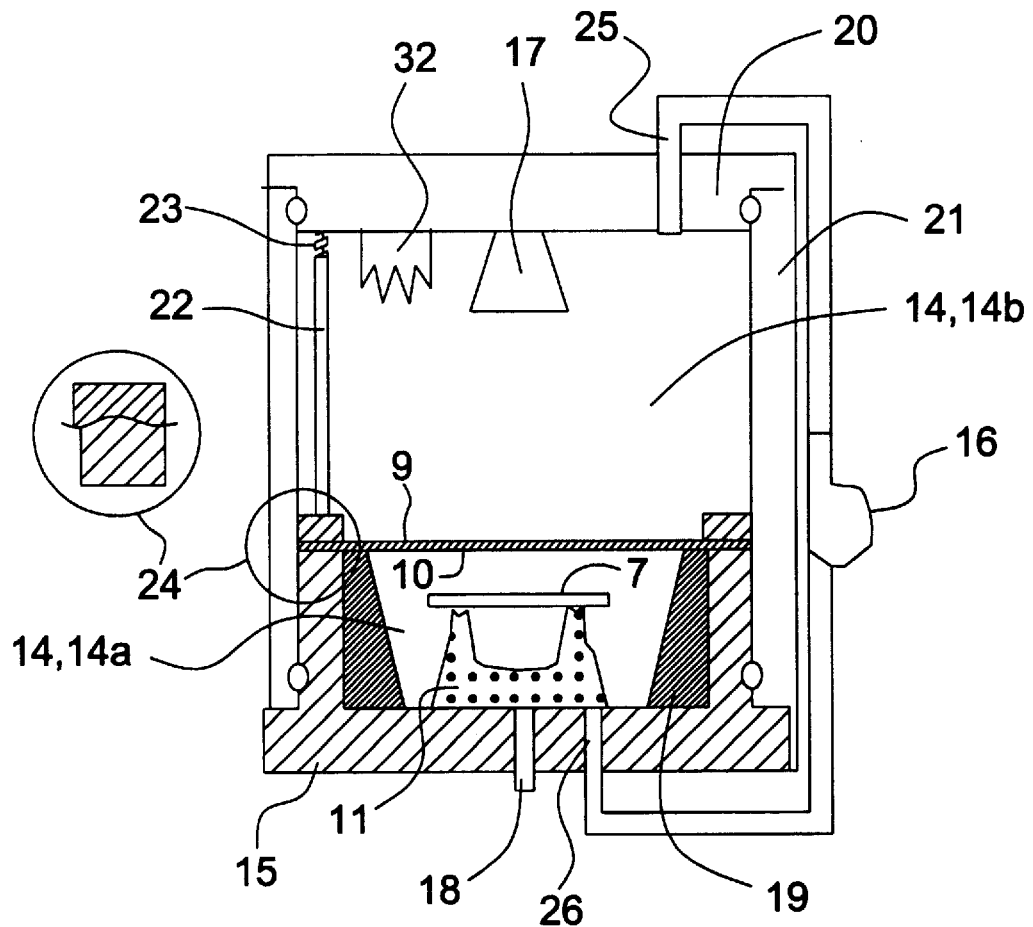
FIG. 4 is a schematic vertical sectional view of a machine according to the invention.
Figure 5:
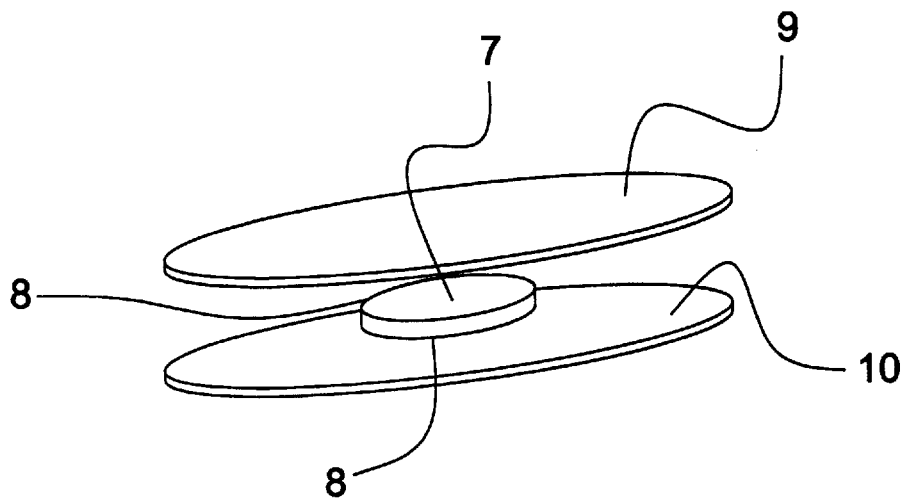
FIG. 5 is a perspective view illustrating the different components of a preimpregnated fabric part according to the invention.

The invention also relates to a machine for implementing the method according to the invention represented in FIG. 4. This machine comprises a sealed enclosure 14, a plate 15 receiving a shaping model 11 in the enclosure 14, a flexible fluid-proof membrane 9, notably air-tight, separating the enclosure 14 into two chambers 14a, 14b, means 16, 25, 26 for creating a lower fluid pressure in the chamber 14a containing the shaping model 11 than in the other chamber 14b, and means 17, 18, 19, 32 for cross-linking the parts 7 placed on the shaping model 11 in the chamber 14a. According to the invention, the cross-linking means 17, 18, 19 are light-curing means comprising at least one light source 17 located in the chamber 14b opposite the one 14a containing the shaping model 11. The flexible separating membrane 9 is then translucent or transparent, i.e. it lets light pass. The cross-linking means 17, 18, 19 comprise at least one light conveying duct 18 giving out onto the receiving plate 15 to light from the inside the shaping model 11 itself made of translucent or transparent material. In this way, lighting from the inside is achieved and the efficiency of the cross-linking is improved. In addition, the cross-linking means 17, 18, 19 can comprise a peripheral mirror 19 surrounding the shaping model 11 to improve the light diffusion.

Instead of, or in combination with the cross-linking means 17, 18, 19, the machine of the invention can comprise chemical and/or thermal cross-linking means 32.

The enclosure 14 is formed by the lower plate 15 receiving the shaping model 11, a similar parallel upper plate 20 forming a cover, and a cylinder 21 placed between these two plates 15, 20 in a fluid-proof manner. The cylinder 21 can be transparent in order to visually monitor the execution of the manufacturing process. The upper plate 20 supports a plurality of small columns 22 with compression springs 23 located at regular intervals on its circumference and designed to press against the peripheral edge of the membrane 9 to wedge it against a cylindrical protuberance 24 of the lower plate 15. The small columns 22, springs 23 and protuberance 24 thus form removable securing means of the membrane 9 separating the two chambers 14a, 14b. The membrane can thus easily be changed as required each time the machine is disassembled, i.e. each time manufacture of a prosthesis is prepared. The lower plate 15 is rigidly associated, in a tight but disassemblable manner, to the cylinder 21 in order to enablechanging of the membrane 9 and/or preparation of the shaping model 11 and of the parts 7 to be polymerized. The light source 17 can be simply formed by an electric light bulb. The pressure difference between the two chambers 14a, 14b can be achieved by inlet of a compressed fluid into the chamber 14b via the orifice and/or by suction of a fluid from the chamber 14a containing the shaping model 11 via a suction orifice 26. For example, the suction orifice 26 and the inlet orifice 25 can be connected to one another by means of a fluid pump 16. Due to the effect of the pressure difference thus achieved, the flexible membrane 9 is pressed against the shaping model 11 and thus presses the pre-impregnated fabric part 7 against this shaping model 11. The lighting means 17, 18 are then switched on causing photo-polymerization of the organic matrix of the preimpregnated fabric part 7 and formation of the support shell 2. The result obtained is represented in FIG. 3. In FIG. 4, the example of manufacture of a denture has been represented. The shaping model 11 is then a laboratory model for a denture. The pre-impregnated fabric part 7 is securely held between two membranes 9, 10. The upper membrane 9 acts as the membrane separating the enclosure 14. Its diameter therefore corresponds to that of the machine. Its thickness can be comprised between 60 and 120 μm. It is formed by an elastic synthetic material such as a copolymer. The lower membrane enables the preimpregnated fabric part 7 to be securely held before the suction means 16 are put into operation. It can also be formed by a translucent membrane of 20 to 40 μm thickness made of copolymer.

The machine according to the invention is compact, particularly simple to manufacture, inexpensive and easy to use. It has thus been possible to achieve such a machine with a height and diameter of about 20 cm.

In practice, a dental crown ready for fitting in the mouth has been able to be achieved from a preimpregnated fabric part 7, including the final stages of polishing and finishing with three layers of cosmetic coating in a time of about 30 minutes. Yet to manufacture a crown of the same nature, the execution times are about 1 hour and 15 minutes for a metallic crown, 1 hour and 30 minutes for a resin crown with metallic armature, and 2 hours for a ceramic crown with metallic armature.

An alternative embodiment of the invention consists in achieving a dental prosthesis wherein the support shell 2 is composed of a composite material comprising an armature 4 made of ceramic fibers sunk in a ceramic powder matrix, and wherein the coating 3 is composed of ceramic powder. Naturally, the composition of the ceramic powder of the matrix and the composition of the ceramic powder of the coating are such that at least one essential component of the ceramic powder of the matrix is of the same as nature as at least one essential component of the ceramic powder of the coating, in compliance with one of the essential features of the invention.

The ceramic powder of the matrix and of the coating can initially include a material acting as a binder. This material can for example be water, alcohol, an organic resin, etc.

This material initially serves the purpose of giving the powder a past consistence suitable for the initial shaping operations.

Furthermore, this material subsequently serves the purpose of giving the powder a final hardness, after baking or polymerization. This material can thus be chosen so as to polymerize in order to harden the proconv. In this case, this material can be a polymerizable organic resin. This material can also be chosen so as to disappear partly or completely when baking is performed. In this case, this material can be water, alcohol, or an organic resin.

We claim:

1. A fabric part preimpregnated with an organic matrix before hardening and covered by an external finishing coating designed to form, after shaping, hardening and depositing of the external finishing coating, a support shell of a dental prosthesis, wherein the orgaanic matrix has at least one essential component of the same nature as at least one essential component of the external finishing coating.

2. The part according to claim 1, wherein the main component(s) of the resin external finishing coating and of the organic matrix are similar.

3. The part according to one of the claim 1 wherein the organic matrix and the external coating finishing are essentially formed by ceramic powder.

4. The part according to claim 1 wherein the organic matrix and the external finishing coating are formed by at least one methacrylate resin.

5. The part according to claim 4, wherein said methacrylate resin is a dimethacrylate resin.

6. The part according to claim 1, wherein the fabric part is composed of at least one layer of fiber-meshed fabric.

7. The part according to claim 1, wherein the fabric armature is composed of a plurality of layers of fiber-meshed fabric.

8. The part according to claim 1, wherein the fabric part is in a general shape of a disk securedly held between two films or membranes.

* * * * *